(12) United States Patent
Yang et al.

(10) Patent No.: US 8,731,342 B2
(45) Date of Patent: May 20, 2014

(54) FIBER-OPTIC SENSOR FOR LIQUID-IMMERSION DETECTION AND FIBER-OPTIC DETECTION SYSTEM FOR LIQUID-IMMERSION DETECTION

(75) Inventors: Chun-Liang Yang, New Taipei (TW); Hsuan-Hung Lin, Taipei (TW)

(73) Assignee: Tamkang University, New Taipei (TW)

( * ) Notice: Subject to any disclaimer, the term of this patent is extended or adjusted under 35 U.S.C. 154(b) by 163 days.

(21) Appl. No.: 13/287,107

(22) Filed: Nov. 1, 2011

(65) Prior Publication Data

US 2012/0281944 A1 Nov. 8, 2012

(30) Foreign Application Priority Data

May 4, 2011 (TW) .............................. 100115696 A

(51) Int. Cl.
*G02B 6/00* (2006.01)
(52) U.S. Cl.
USPC .................................. 385/12; 385/13; 385/88
(58) Field of Classification Search
USPC ..................... 385/12, 13, 31, 39, 88
See application file for complete search history.

(56) References Cited

U.S. PATENT DOCUMENTS

| 5,402,508 A * | 3/1995 | O'Rourke et al. ............... 385/31 |
| 5,625,459 A * | 4/1997 | Driver ........................... 356/446 |
| 7,068,878 B2 * | 6/2006 | Crossman-Bosworth et al. ............................... 385/25 |
| 7,821,620 B2 * | 10/2010 | Dogariu .......................... 356/39 |
| 2004/0251405 A1 * | 12/2004 | Yankielun ................ 250/227.14 |
| 2011/0281231 A1 * | 11/2011 | Rizoiu et al. ..................... 433/29 |
| 2012/0282566 A1 * | 11/2012 | Rizoiu et al. ..................... 433/29 |

OTHER PUBLICATIONS

Shoji Adachi, "Distributed Optical Fiber Sensors and Their Applications", SCIE Annual Conference 2008, Aug. 20-22, 2008, 329-333.
SST Sensing Ltd, "Optical Liquid Level Sensor Operating Principle", Application Note, 2009, 1~3.
Nakazawa et al., "Technologies for Checking Outside Optical Distribution Equipment", NTT Technical Review, vol. 7, No. 11, Nov. 2009, 1~6.

* cited by examiner

*Primary Examiner* — Ellen Kim
(74) *Attorney, Agent, or Firm* — Jianq Chyun IP Office

(57) ABSTRACT

A fiber-optic sensor for liquid-immersion detection includes an optical fiber and an interface material layer. The optical fiber has an angled physical contact (APC) surface. The interface material layer contacts with the APC surface. The interface material layer has a rough surface when in a dry state to produce a diffusion reflection. The interface material layer has a smooth surface to produce a specular reflection when the interface material layer absorbs a liquid in a wet state.

7 Claims, 4 Drawing Sheets

FIBER-OPTIC SENSOR FOR LIQUID-IMMERSION DETECTION AND FIBER-OPTIC DETECTION SYSTEM FOR LIQUID-IMMERSION DETECTION

CROSS-REFERENCE TO RELATED APPLICATION

This application claims the priority benefit of Taiwan application serial no. 100115696, filed on May 4, 2011. The entirety of the above-mentioned patent application is hereby incorporated by reference herein and made a part of this specification.

BACKGROUND OF THE INVENTION

1. Field of the Invention

The invention relates to a fiber-optic sensor for liquid-immersion detection configured to detect the dry/wet state of the environment which the sensor is in, for example.

2. Description of Related Art

Recently, the capacity of data transmission has increased rapidly with the flourishing development in the internet, where pictures and images of high quality occupy a large portion of the bandwidth. As a consequence, the usage rate of optical fibers increases significantly. Triple-play service including voice, data and image provided through optical fiber network has gradually become the mainstream method for transmission.

Since optical fiber network has extended to a wide range, the water immersion occurring on the optical fiber communication wiring or the cable wiring at joint box, roadside cabinets, or portion at underground duct needs to be detected in real time for technicians to eliminate the water immersion.

A typical commercial product includes a liquid level sensor which is mainly disposed in a sensor of a single location. The surface of the sensor is easily affected by external environmental factors (i.e. dust), and the function of the sensor is thus influenced thereby, which makes the sensor not fit to be disposed on the optical fiber detection wiring. Although other sensors have been proposed for detecting the water immersion of the optical fiber wiring, the sensing mechanism here is to use a non-woven cloth to absorb water, where the non-woven cloth swells so that the optical fiber results in bending loss, and to observe with an optical time domain reflectometer (OTDR). Nevertheless, the bending loss of this sensor is as high as 10 dB when immersed by water, such that the water immersions occurring at multiple locations can not be observed on the OTDR at the same time. Moreover, the subsequent detection wiring may easily break down due to the breakage of one of the detection points.

Therefore, researches have been carried out for efficient detection of the water immersions on optical fiber network.

SUMMARY OF THE INVENTION

The invention relates to a fiber-optic sensor for liquid-immersion detection capable of disposing a plurality of detection points on an optical fiber network easily and effectively to rapidly and accurately detect whether or not liquid-immersion has occurred in the optical fiber network, such as the occurrence of water immersion.

The invention relates to a fiber-optic sensor for liquid-immersion detection, which includes an optical fiber and an interface material layer. The optical fiber has an angled physical contact (APC) surface. The interface material layer contacts the APC surface of the optical fiber. The interface material layer has a rough surface to produce a diffusion reflection when in a dry state. The interface material layer has a smooth surface to produce a specular reflection when absorbed a liquid in a wet state.

The invention is also directed to a fiber-optic detection system for liquid-immersion detection, which includes an optical time domain reflectometer (OTDR), a backbone optical fiber, an optical splitter, and a fiber-optic sensor for liquid-immersion detection. The backbone optical fiber is coupled to the OTDR. The optical splitter is disposed on the backbone optical fiber to split a detection light. The fiber-optic sensor for liquid-immersion detection is coupled to the optical splitter through a branch optical fiber. The fiber-optic sensor for liquid-immersion detection includes an optical fiber and an interface material layer. The optical fiber has one end coupled to the branch optical fiber and the other end with an APC surface. The interface material layer contacts the APC surface of the optical fiber. The interface material layer has a rough surface to produce a diffusion reflection when in a dry state. The interface material layer has a smooth surface to produce a specular reflection when absorbed a liquid in a wet state. The detection light output from the optical splitter generates an optical power difference through a difference between the diffusion reflection and the specular reflection when being reflected back to the OTDR to identify whether the interface material layer is in the dry state or the wet state.

In order to make the aforementioned and other features and advantages of the invention more comprehensible, several embodiments accompanied with figures are described in detail below.

BRIEF DESCRIPTION OF THE DRAWINGS

The accompanying drawings provide further understanding and constitute a part of this specification. The drawings illustrate embodiments and, together with the description, serve to explain the principles of the invention.

DESCRIPTION OF EMBODIMENTS

The invention proposes that a fiber-optic sensor for liquid-immersion detection can be applied in a fiber-optic detection system for liquid-immersion detection. Together with the use of an optical time domain reflectometer (OTDR), liquid-immersions at multiple locations can be observed at the same time. A detection wiring here adopts a branching design, such that the operations of other detection points and a backbone optical fiber detection wiring are not affected by the breakdown of a detection point or the breakage of a branch optical fiber. When a branch detection point is damaged or immersed by a liquid, a sensor module can be simply detached and replaced with easy operation and maintenance.

Once the backbone optical fiber detection wiring has been laid out, an optical splitter and the fiber-optic sensor for liquid-immersion detection can then be disposed according to the needs of detection locations. Thereafter, the OTDR can be used to examine the state of each of the fiber-optic sensor for liquid-immersions detection in real time.

Since the water immersion occurring on the optical fiber transmission wirings or cable wirings at roadside cabinets, or portion at underground duct is quite often, the immersion by any liquid can cause damages. Therefore, the immersion by water is merely one embodiment adopted in the invention.

In the following, several embodiments are provided to describe the invention; however, the invention is not limited to thereto.

Figure 1A:
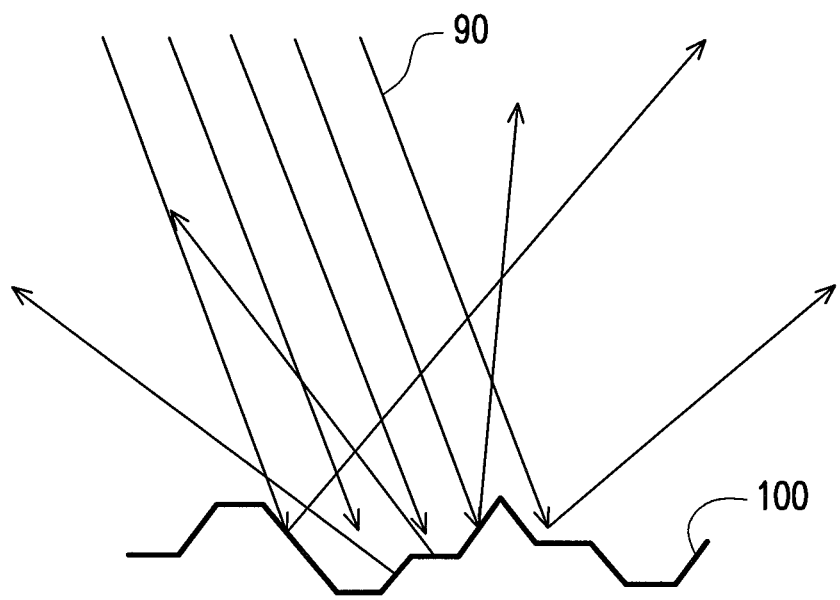
FIGS. 1A-1B are schematic diagrams illustrating an operational mechanism of a fiber-optic sensor for water-immersion detection in the invention.
Figure 1B:
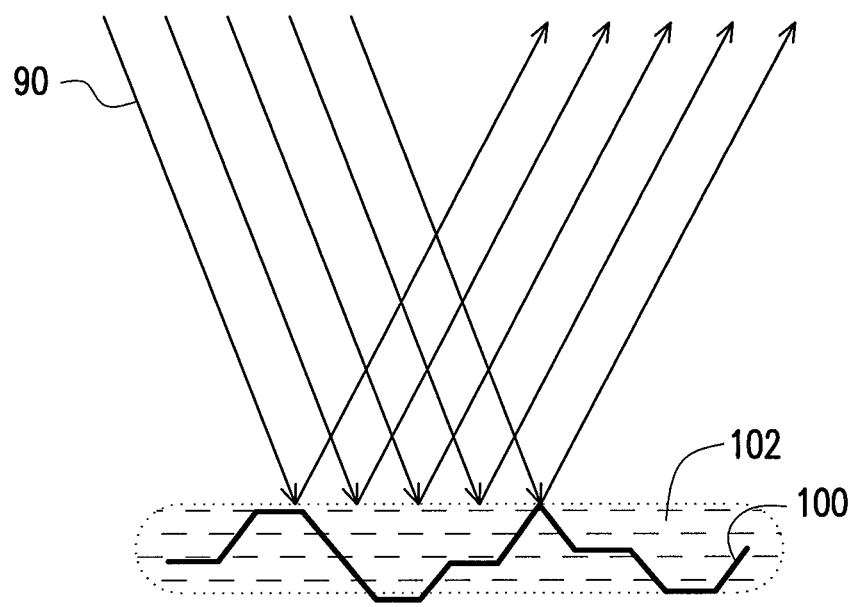

An operational mechanism of the invention is illustrated first. FIGS. 1A-1B are schematic diagrams illustrating an operational mechanism of a fiber-optic sensor for water-immersion detection in the invention. Referring to FIG. 1A, an interface material 100 similar to a sponge material, for example, a melamine sponge has a rough structure at a dry state. Owing to the slightly rough surface, when an incident light 90 enters the rough surface, the reflected light has a diffusion reflection which is also referred as a scattering reflection, where the reflected light does not reflect in a particular direction.

Referring to FIG. 1B, when the interface material 100 absorbs a liquid 102, for example, absorbs water, the liquid 102 fills the rough structure of the interface material 100 and turns into a smooth surface, for example, a structure approximating to a specular surface. At this time, the incident light 90 is reflected like a reflection phenomenon by a conventional specular surface after entering this smooth surface, for instance, and this is referred as a specular reflection.

Through the reflection difference between the diffusion reflection and the specular reflection, whether the interface material 100 is immersed by water or not can be detected by the difference in the intensity of the reflected light coupled the APC surface of the optical fiber.

Figure 2:
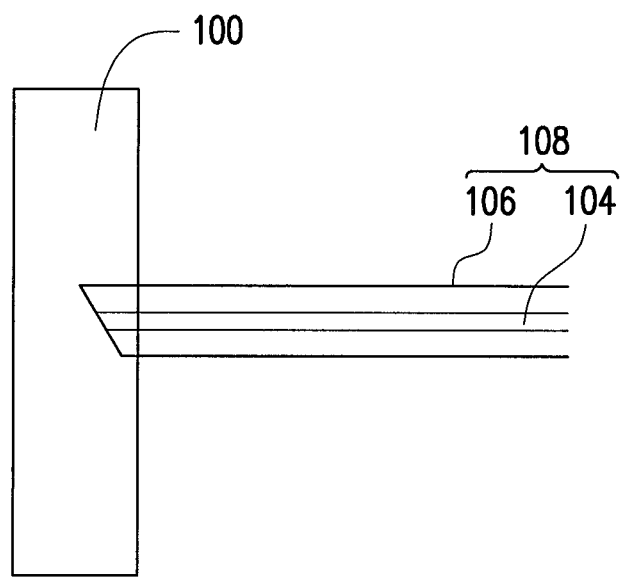
FIG. 2 is a schematic diagram showing a basic framework of a fiber-optic sensor for water-immersion detection according to an embodiment of the invention.

FIG. 2 is a schematic diagram showing a basic framework of a fiber-optic sensor for water-immersion detection according to an embodiment of the invention. Referring to FIG. 2, in the invention, a detection mechanism is established based on the theories of the specular reflection and the diffusion reflection of the interface material 100, so that the interface material 100 can be utilized as a sensing device for determining whether the water immersion has occurred. On the other hand, the fiber-optic sensor for water-immersion detection is also coupled to the interface material 100 in cooperation with an optical fiber 108 having the APC surface. The optical fiber 108 includes an optical fiber core layer 104 and an optical fiber cladding layer 106. The transmission of a light signal is achieved by the reflection of light at an interface of the optical fiber core layer 104 and the optical fiber cladding layer 106. One end of the optical fiber 108 contacting the interface material 100 has the APC structure, for example, with the design of an 8° angle.

When the sensor is not immersed by water, the detection light displays a diffusion reflection characteristic after passing through the 8° APC surface via the optical fiber and then reflected by the interface material 100. At this time, the reflected light has a higher probability of re-entering the optical fiber interface. Consequently, the reflection rate is higher, and the height of the reflection pulse is also higher. When the interface material 100 of the sensor is immersed by water, the specular reflection is generated on the 8° APC surface. Owing to the design of the 8° APC surface and the specular reflection characteristic of the sensing interface, the reflected light has a lower probability of re-entering the optical fiber 108. Accordingly, the reflection damage is greater, and the height of the reflection pulse is lower. Here, the angle of the optical fiber having the APC surface is not limited to 8° as long as the two states can be identified.

Figure 3:
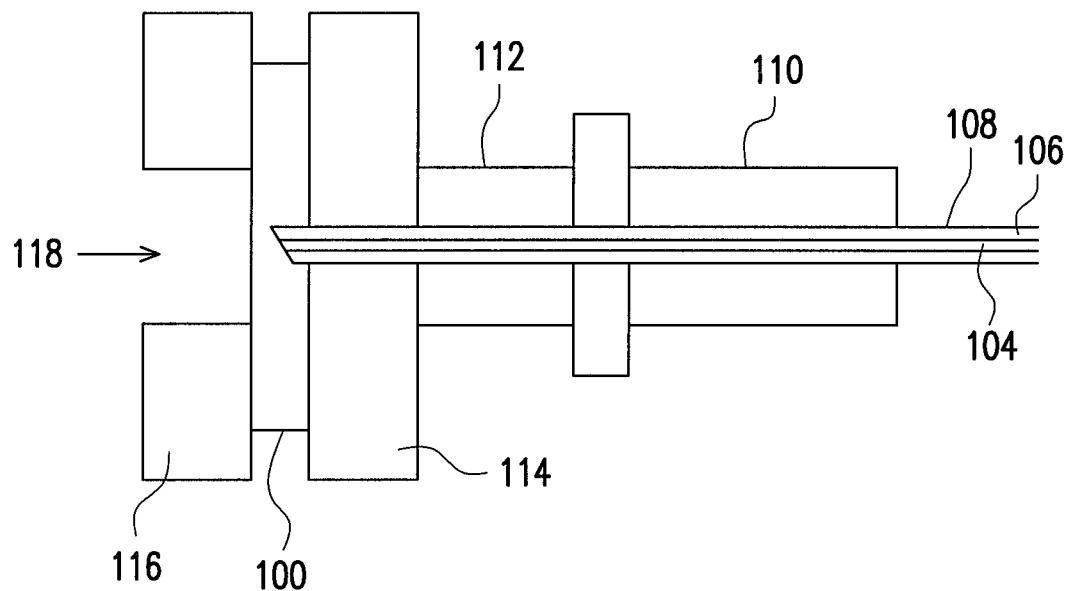
FIG. 3 is a schematic cross-sectional diagram showing a framework of a fiber-optic sensor for water-immersion detection according to an embodiment of the invention.

FIG. 3 is a schematic cross-sectional diagram showing a framework of a fiber-optic sensor for water-immersion detection according to an embodiment of the invention. Referring to FIG. 3, a conventional optical fiber connector 110 and a ferrule 112 are combined, so that the optical fiber 108 having the APC surface contacts the interface material 100. The interface material 100 applied a connection base structure to contact the APC surface of the optical fiber 108. The connection base structure is constituted by two carriers 114, 116, for example, and the interface material 100 is sandwiched therebetween. The carrier 116 can further have an inlet hole formed therein for allowing liquids from the external environmental to enter. For example, when the local environment has been immersed by water, water is absorbed by the interface material 100 from the inlet hole 118 to generate the specular reflection. The sensor can be disposed in any location that needs to be detected. The structure of the sensor is simple and light, easy for technicians to perform maintenance and replacement. The APC surface of the optical fiber connector constitutes an angled sensing interface with a water transmissive-diffusion reflection medium.

Figure 4:
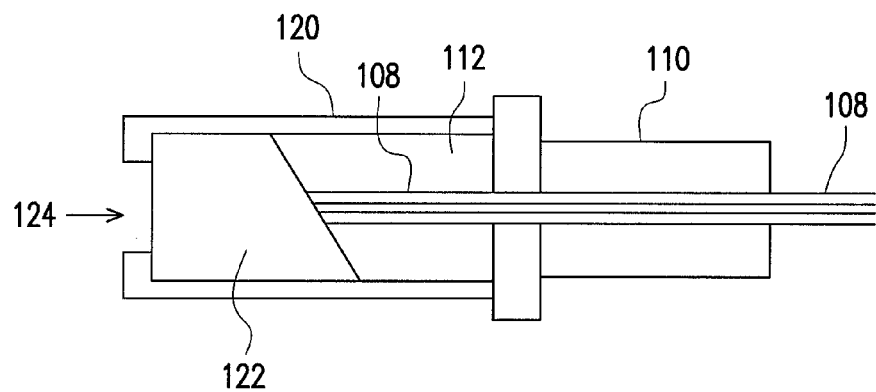
FIG. 4 is a schematic cross-sectional diagram showing a framework of a fiber-optic sensor for water-immersion detection according to another embodiment of the invention.

FIG. 4 is a schematic cross-sectional diagram showing a framework of a fiber-optic sensor for water-immersion detection according to another embodiment of the invention. Referring to FIG. 4, FIG. 4 is similar to the framework of that of FIG. 3; however, the structure for disposing the interface material 100 is different from that in FIG. 3. In this embodiment, the optical fiber in the ferrule 112 still contacts an interface material 122 with the same angle. Nonetheless, the interface material 122 is fixed by using another external ferrule 120, for instance, a metal ferrule fixes the interface material 122 with the ferrule 120. The external ferrule 120 also has an inlet hole 124 allowing liquids to be absorbed by the interface material 122 to generate the specular reflection.

Here, the metal ferrule is adopted as a head end of the fiber-optic sensor for water-immersion detection. As a consequence, the fiber-optic sensor for water-immersion detection becomes more compact. A method of fabricating the sensor includes the following. The water transmissive-diffusion reflection medium is placed into the metal ferrule, which is then tightly connected to the APC surface of the optical fiber connector. The water transmissive-diffusion reflection medium shows different reflections under the dry or wet state, that is, the diffusion reflection and the specular reflection so as to determine the occurrence of water immersion with the height difference of the reflection pulses.

The fiber-optic sensor for water-immersion detection can be disposed at any locations of the backbone optical fiber that need to be detected, and the number of the sensors is also determined according to needs. The fiber-optic sensor for water-immersion detection is generally a fiber-optic sensor for liquid-immersion detection; however, the sensor is not limited to detect water immersion.

Shown in the verification from the experiments, the difference in optical power between the two states can be greater than 3 dB.

Figure 5:
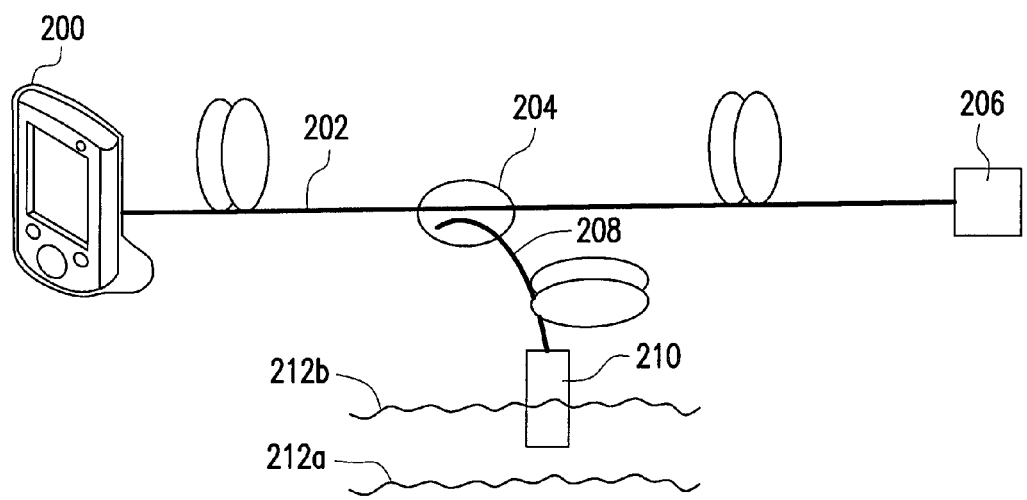
FIG. 5 depicts a schematic diagram of a fiber-optic detection system for liquid-immersion detection according to an embodiment of the invention.

FIG. 5 depicts a schematic diagram of a fiber-optic detection system for liquid-immersion detection according to an embodiment of the invention. Referring to FIG. 5, one of a plurality of fiber-optic sensors for water-immersion detection of a backbone optical fiber is illustrated as an example.

A fiber-optic detection system for liquid-immersion detection includes an OTDR 200, a backbone optical fiber 202, an optical splitter 204, a branch optical fiber 208, and a fiber-optic sensor 210 for liquid-immersion detection. The backbone optical fiber 202 is coupled to the OTDR 200. The OTDR 200 emits a continuous optical pulse signal and simultaneously detects whether or not an environmental liquid has immersed the fiber-optic sensor 210 for liquid-immersion detection. The d dry/wet state indicated on the OTDR 200 is of a reflection signal from the fiber-optic sensor 210 for liquid-immersion detection. The optical splitter 204 is disposed on the backbone optical fiber 202 to split a portion of the light as the detection light. An endpoint of the backbone optical fiber 202 has a terminator 206. The branch optical fiber 208 is coupled to the optical splitter 204 to receive the detection light and therefore transmit the light signal. The fiber-optic sensor 210 for liquid-immersion detection is coupled to the branch optical fiber 208. The fiber-optic sensor 210 for liquid-immersion detection, as aforementioned, includes an optical fiber, one end coupled to the branch optical fiber 208, and the other end having an APC surface. The interface material layer contacts the APC surface of the optical fiber.

According to the descriptions in FIGS. 2-4, the interface material layer has a rough surface in a dry state, thereby generating a diffusion reflection. When a liquid is absorbed, the interface material layer is in a wet state and has a smooth surface to generate a specular reflection.

The detection light output from the optical splitter 204 generates an optical power difference through a difference between the diffusion reflection and the spectacular reflection when being reflected back to the OTDR to identify whether the interface material layer is in the dry state or the wet state. A path of the reflected light also goes through the branch optical fiber 208, the optical splitter 204, the backbone optical fiber 202 to reach the OTDR so as to shown the reflection pulse. When the interface material layer is in a water-immersed state, the reflection pulse greatly decreases or vanishes.

In the detection of water level, for instance, a water level 212a usually does not reach a height disposed with the fiber-optic sensor 210 for liquid-immersion detection. However, when the environment changes so that a water level 212b rises to the height that the fiber-optic sensor 210 for liquid-immersion detection is disposed at, the reflection pulse on the OTDR 200 vanishes to notify the rising of the water level 212b.

Figure 6:
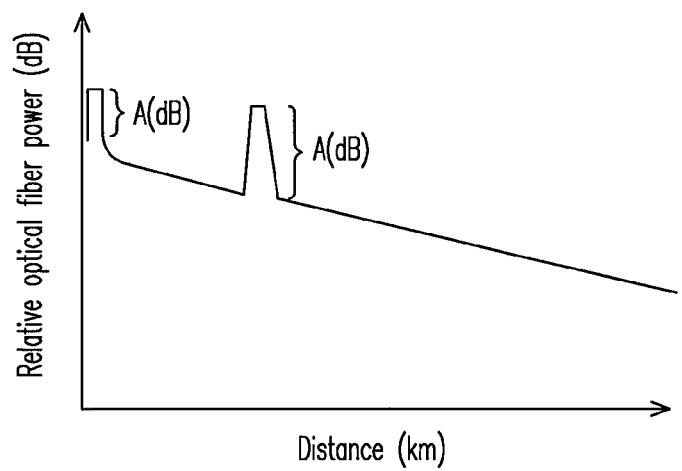
FIG. 6 is a schematic diagram illustrating a change in a relative optical fiber power of a backbone optical fiber with distance.

A plurality of fiber-optic sensors for liquid-immersion detection is generally disposed at different locations on one backbone optical fiber. Since the light damage of the optical fiber increases with distance, the sensing level of the fiber-optic sensor for liquid-immersion detection also has to be adjusted. In the invention, a method of estimating the reflection pulse is proposed. FIG. 6 is a schematic diagram illustrating a change in a relative optical power of a backbone optical fiber with distance. Referring to FIG. 6, according to the disposition shown in FIG. 5, the change in the relative optical power is in units of dB. The fiber-optic sensor for liquid-immersion detection generates a pulse in the dry state. The height of the pulse relative to the baseline is represented with A, which can be illustrated using an Equation (1):

$$A(\text{dB}) = 5 \cdot \log_{10}\left[\frac{R_{end}}{(1+SR^2) \cdot B} + 1\right], \quad (1)$$

Herein, $R_{end}$ is a reflection coefficient of the fiber-optic sensor for liquid-immersion detection on the branch optical fiber; $SR^2$ is the square of an optical splitting ratio of the backbone optical fiber to the branch optical fiber in the optical splitter; B is a backscatter factor of the optical fiber, depending on an operation wavelength and a pulse width of the detection light emitted by the OTDR. In Equation (1), $SR^2$ in the optical splitter is an adjustable parameter according to the requirements for implementing the fiber-optic detection system.

Figure 7:
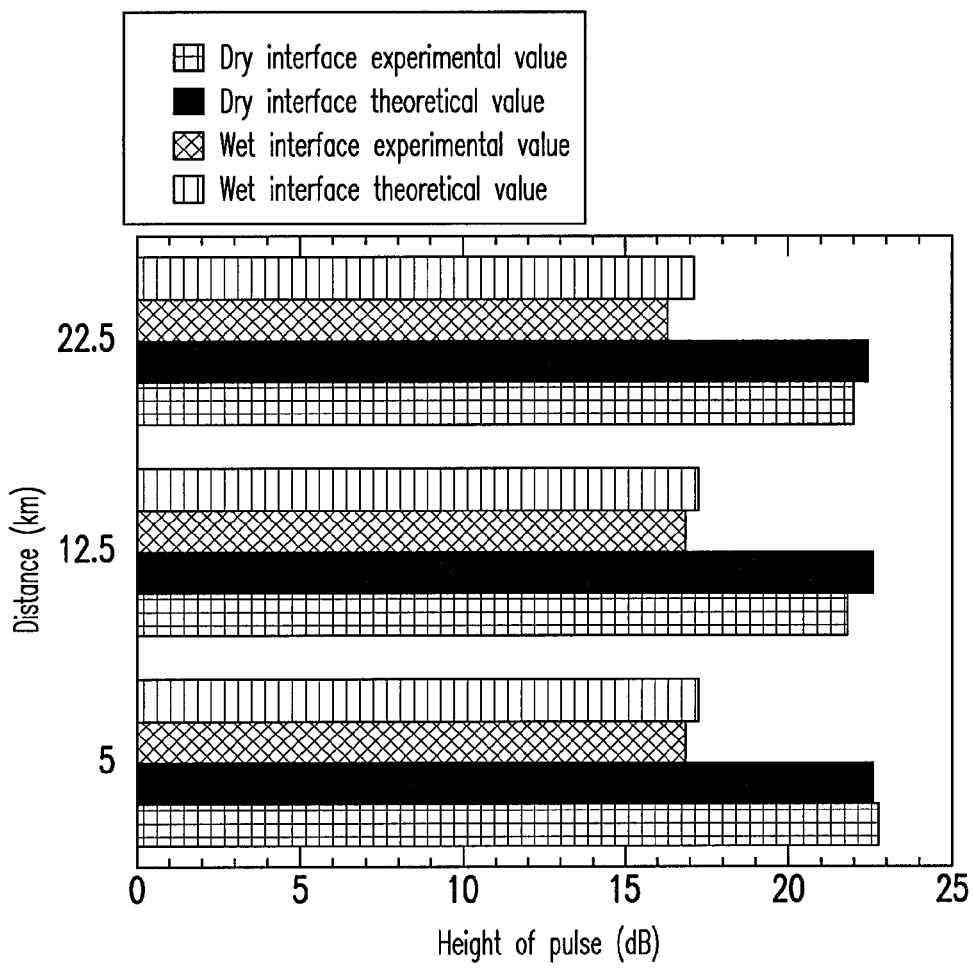
FIG. 7 is a schematic diagram showing a verifying result from an experiment and an estimation of Equation (1) according to an embodiment of the invention.

FIG. 7 is a schematic diagram showing a verifying result from an experiment and an estimation of Equation (1) according to an embodiment of the invention adopting an optical fiber connector having a physical contact to replace the fiber-optic sensor for liquid-immersion detection. Referring to FIG. 7, though the distances are different, values of the reflection pulse estimated using Equation (1) correspond to the experimental results. The difference in the height of the reflection pulses is sufficient to distinguish the dry state and the wet state. In FIG. 7, solid bars are dry interface theoretical values and square block bars are dry interface experimental values. Moreover, bars with horizontal lines are wet interface theoretical values and bars with diamonds are wet interface experimental values.

The sensor device provided in the invention has a simple framework, low cost, and capability of performing unambiguous identification. In comparison, the traditional framework is more complicated and not easy for maintenance and replacement. The conventional module thereof is larger and not suitable for distant detection. The cost of the traditional framework is also higher than the sensor designed herein.

It will be apparent to those skilled in the art that various modifications and variations can be made to the structure of the disclosed embodiments without departing from the scope or spirit of the invention. In view of the foregoing, it is intended that the invention cover modifications and variations of this invention provided they fall within the scope of the following claims and their equivalents.

What is claimed is:

1. A fiber-optic detection system for liquid-immersion detection, comprising:
   an optical time domain reflectometer;
   a backbone optical fiber coupled to the optical time domain reflectometer;
   an optical splitter disposed on the backbone optical fiber to split a detection light;
   a branch optical fiber coupled to the optical splitter and receiving the detection light; and
   a fiber-optic sensor for liquid-immersion detection, coupled to the branch optical fiber, the fiber-optic sensor for liquid-immersion detection comprising:
      an optical fiber having one end coupled to the branch optical fiber and the other end comprising an angled physical contact surface; and
      an interface material layer contacting the angled physical contact surface of the optical fiber, wherein the interface material layer has a rough surface to produce a diffusion reflection when in a dry state and a smooth surface to produce a specular reflection when absorbed a liquid in a wet state,
   wherein the detection light output from the optical splitter generates an optical power difference through a difference between the diffusion reflection and the specular reflection when being reflected back to the optical time domain reflectometer to identify whether or not the interface material layer is in the dry state or the wet state.

2. The fiber-optic detection system for liquid-immersion detection as claimed in claim 1, wherein the liquid absorbed by the interface material layer is water.

3. The fiber-optic detection system for liquid-immersion detection as claimed in claim 1, wherein the interface material layer comprises a melamine sponge.

4. The fiber-optic detection system for liquid-immersion detection as claimed in claim 1, wherein when the branch optical fiber receives the detection light entering the interface material layer from the angled physical contact surface, the branch optical fiber receives a first optical reflection level and a second optical reflection level of different degrees through the difference between the diffusion reflection and the specular reflection.

5. The fiber-optic detection system for liquid-immersion detection as claimed in claim 1, further comprising a connection base structure to couple the angled physical contact surface of the optical fiber and the interface material layer, wherein the connection base structure has a liquid entry hole for the liquid to enter the interface material layer.

6. The fiber-optic detection system for liquid-immersion detection as claimed in claim 1, wherein the optical splitter has a splitting ratio to determine a degree of a difference in optical power of the interface material layer in the dry state and the wet state.

7. The fiber-optic detection system for liquid-immersion detection as claimed in claim 1, wherein an operation of the optical splitter is set a condition to produce a signal pulse height (A) in the dry state under an operation wavelength, wherein A is estimated according to:

$$A(\text{dB}) = 5 \cdot \log_{10}\left[\frac{R_{end}}{(1+SR^2) \cdot B} + 1\right],$$

in which $R_{end}$ is a reflection coefficient of the fiber-optic sensor for liquid-immersion detection on the branch optical fiber; $SR^2$ as an adjustable parameter for setting the condition is a square of an optical splitting ratio of the backbone optical fiber to the branch optical fiber in the optical splitter; B is a backscatter factor of the optical fiber.

* * * * *